United States Patent [19]

Alpegiani et al.

[11] Patent Number: 4,623,643

[45] Date of Patent: Nov. 18, 1986

[54] PENEM DERIVATIVES

[75] Inventors: Marco Alpegiani; Angelo Bedeschi; Maurizio Foglio; Giovanni Franceschi; Ettore Perrone, all of Milan, Italy

[73] Assignee: Farmitalia Carlo Erba S.p.A., Milan, Italy

[21] Appl. No.: 742,859

[22] Filed: Jun. 10, 1985

Related U.S. Application Data

[63] Continuation-in-part of Ser. No. 481,924, Apr. 4, 1983, Pat. No. 4,577,016.

[30] Foreign Application Priority Data

Jun. 29, 1984 [GB] United Kingdom ............... 8416652

[51] Int. Cl.⁴ ............... C07D 499/00; A61K 31/425
[52] U.S. Cl. .................................... 514/196; 540/310
[58] Field of Search .............. 260/245.2 T, 245.2 R; 514/196

[56] References Cited

U.S. PATENT DOCUMENTS 4,482,565  11/1984  Foglio et al. ............... 260/245.2 T Primary Examiner—Nicholas S. Rizzo
Attorney, Agent, or Firm—Oblon, Fisher, Spivak, McClelland & Maier

[57] ABSTRACT

Penem derivatives are disclosed characterized by a substituted pyridiniomethyl group in the 2-position of the penem nucleus. The compounds of the present application exhibit better antibacterial activity than other known penem derivatives.

7 Claims, No Drawings

PENEM DERIVATIVES

CROSS-REFERENCE TO RELATED APPLICATION

This application is a continuation-in-part application of our copending U.S. patent application Ser. No. 481,924 filed Apr. 4, 1983, now U.S. Pat. No. 4,557,016.

DESCRIPTION OF THE INVENTION

The present invention is directed to a narrow class of compounds within the broad disclosure of the parent application Ser. No. 481,924, to a process for their preparation, and to pharmaceutical and veterinary compositions containing them. The compounds of the present, selection invention are the compounds of the following general formula (I)

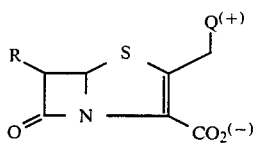

wherein

R is a $C_1$–$C_3$ alkyl group substituted by a free or protected hydroxy;

$Q^{(+)}$ represents a group

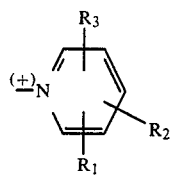

wherein $R_1$ is a substituent selected from the group consisting of (a) halogen; (b) hydroxy; (c) $C_1$–$C_4$ alkoxy; (d) $C_1$–$C_4$ alkylthio; (e) a group

wherein each of $R_4$ and $R_5$ is, independently, hydrogen or $C_1$–$C_4$ alkyl; (f) sulfo; (g) —$CO_2R_4$ wherein $R_4$ is as defined above; (h) —C≡N; (i) dimethylformimidino [—N═CH—N(CH$_3$)$_2$]; (j) a group

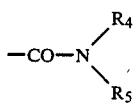

wherein $R_4$ and $R_5$ are as defined above; (k) carbamoyloxy; (l) a hydroxyminomethyl (HO—N═CH—) or methoxyminomethyl (CH$_3$O—N═CH—) group; (m) a formamido or acetamido group; (n) a formyloxy or acetoxy group; (o) a $C_1$–$C_4$ alkanoyl group; (p) an aryl group; (q) a saturated or unsaturated heterocyclic ring; and (r) a $C_1$–$C_4$ alkyl group either unsubstituted or substituted by a substituent chosen from (a) to (q) above; each of $R_2$ and $R_3$ is, independently, hydrogen or one of the groups (a) to (r) defined above, provided that, when $R_2$ and $R_3$ are both hydrogen, then $R_1$ is not a group

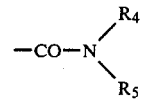

wherein $R_4$ and $R_5$ are both hydrogen; and the pharmaceutically or veterinarily acceptable salts thereof.

The present invention includes all the possible isomers, including geometrical and optical isomers, of the compounds of formula (I), either in the form of isomeric mixtures or in the form of the individual separated isomers. Preferably, the compounds of formula (I) have the (5R,6S) configuration. The preferred group R is the (α-hydroxy)ethyl group which preferably has a (1R) configuration, i.e. a R configuration at the α-carbon atom of the ethyl group. As already said, also the pharmaceutically or veterinarily acceptable salts of the compounds of formula (I) are included within the scope of the invention. The said salts may be both salts with acids, either inorganic acids such as, e.g., hydrochloric or sulphuric acid, or organic acids such as, e.g., acetic, citric, tartaric, fumaric or methanesulphonic acid, and salts with bases, either inorganic bases such as, e.g., alkali or alkaline-earth metal hydroxides, in particular sodium and potassium hydroxides, or organic bases such as, e.g., triethylamine, pyridine, benzylamine or collidine, including aminoacids such as, e.g. lysine or procaine. The invention includes also inner salts, i.e. zwitterions. The alkyl groups, including the aliphatic moieties of the alkoxy, alkylthio and alkanoyl groups, may be branched or straight chain.

In the present specification, the term "halogen" preferably encompasses fluorine and chlorine atoms, but also iodine and bromine atoms.

The term "aryl" encompasses, preferably, phenyl and naphthyl groups, in particular unsubstituted phenyl, α-naphthyl and β-naphthyl groups. A heterocyclic ring may be, as already said, saturated or unsaturated, may have from 4 to 7 members and may contain from 1 to 4 heteroatoms selected from oxygen, nitrogen and sulphur atoms. It is, preferably, a saturated or unsaturated pentatomic or hexatomic heteromonocyclic ring containing 1 to 4 heteroatoms chosen from oxygen, nitrogen and sulphur. Specific examples of preferred heterocyclics are furyl, in particular 2-furyl, thienyl, in particular 2-thienyl, or pyridyl, in particular 2-pyridyl or 3-pyridyl.

A $C_1$–$C_3$ alkyl group is, preferably, ethyl.

A $C_1$–$C_4$ alkyl group is, preferably, methyl or ethyl.

A $C_1$–$C_4$ alkoxy group is, preferably, methoxy or ethoxy.

A $C_1$–$C_4$ alkylthio group is, preferably, methylthio or ethylthio.

A $C_1$–$C_4$ alkanoyl group is, preferably, acetyl or propionyl. A protected hydroxy group may be a hydroxy group protected by a protecting group chosen, for instance, from an optionally substituted, especially halo-substituted, acyl group, e.g., acetyl, monochloroacetyl, dichloroacetyl, trifluoroacetyl, benzoyl or p-bromophenacyl; a triarylmethyl group, in particular triphenylmethyl; a silyl group, in particular trimethylsilyl, dimethyl-tert-butylsilyl, diphenyl-tert-butyl silyl; or also a group such as tert-butoxy carbonyl, p-nitrobenzyloxycarbonyl, 2,2,2,-trichloroethoxycarbonyl, allyloxycarbonyl, benzyl, and pyranyl. Preferred protecting groups of the hydroxy function are p-nitrobenzyloxycarbonyl; dimethyl-tert-butyl-silyl; diphenyl-tert-butyl-silyl; trimethyl silyl; allyloxycarbonyl; benzyl; p-bromo-phenacyl; triphenylmethyl and pyranyl.

A preferred class of compounds under this invention includes compounds of formula (I) wherein R is an (α-hydroxy)-ethyl group and $Q^{(+)}$ is one of the following groups

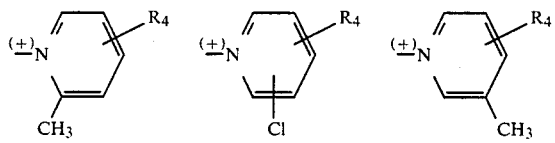

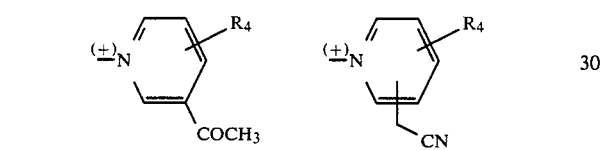

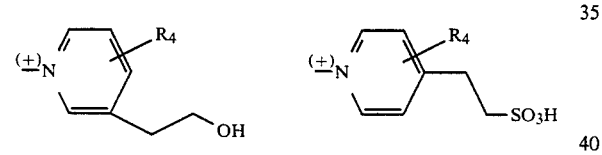

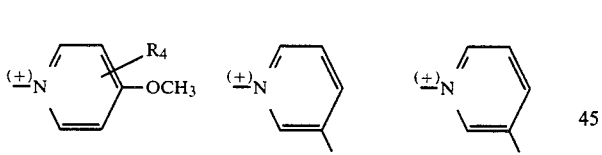

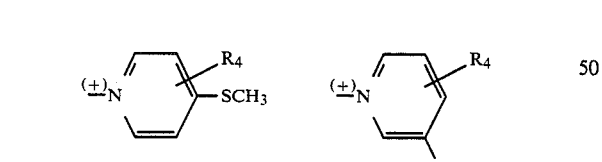

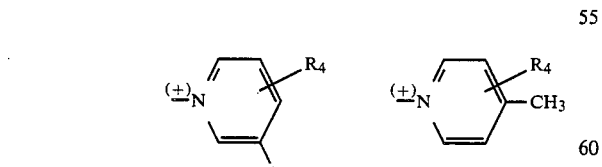

wherein $R_4$ is hydrogen or $C_1$–$C_4$ alkyl, and the pharmaceutically or veterinarily acceptable salts thereof.

Specific examples of preferred compounds of the invention are those listed in the following table

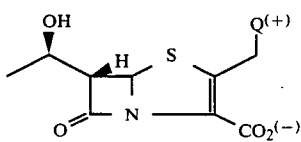

| Compound | $Q^{(+)}$ |
|---|---|
| 1 | 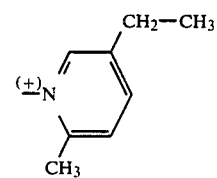 |
| 2 | 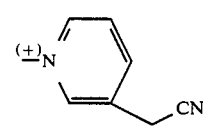 |
| 3 | 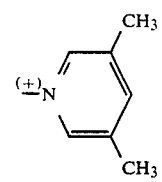 |
| 4 | 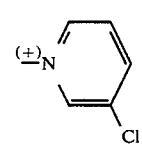 |
| 5 | 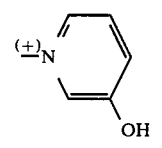 |
| 6 | 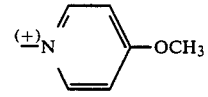 |
| 7 | 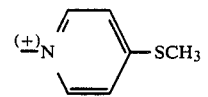 |
| 8 | 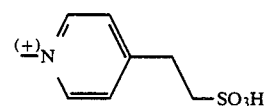 |
| 9 | 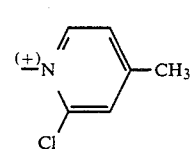 |

-continued

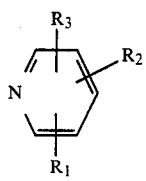

| Compound | $Q^{(+)}$ |
|---|---|
| 10 | 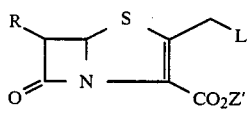 |
| 11 | 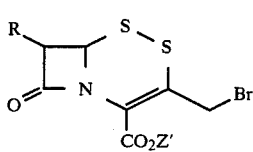 |
| 12 | 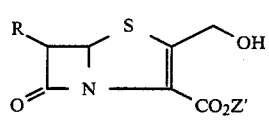 |

The compounds of formula (I) are prepared by a process comprising reacting a compound of formula (II)

$$\text{(II)}$$

wherein $R_1$, $R_2$ and $R_3$ are as defined above, either with a penem intermediate of formula (III)

$$\text{(III)}$$

wherein R is as defined above, Z' is a carboxy protecting group, and L is a leaving group susceptible of nucleophilic displacement by the reagent (II), or with a 2-thiacephem derivative of formula (IV)

$$\text{(IV)}$$

wherein R and Z' are as defined above and, where necessary or desired, removing the protecting groups present in the product of the reaction between the compound (II) and the compound (III) or, in any order, desulphurizing the product of the reaction between the compound (II) and the compound (IV) and removing the protecting groups therein present, and, if desired, converting an obtained compound into a salt thereof and/or, if desired, separating a mixture of isomers into the single isomers.

The leaving group L in the compound of formula (III) may be, for example, a sulphonyloxy group, preferably trifluoromethanesulphonyloxy ($—O—SO_2CF_3$), or a halogen atom, preferably chlorine, bromine or iodine.

A carboxy protecting group Z' may be any group which, together with the $—CO_2—$ moiety, forms an esterified carboxy group. Examples of carboxy protecting groups are, in particular, unsubstituted $C_1$-$C_6$ alkyl groups, for instance methyl, ethyl or tert-butyl; halo-substituted $C_1$-$C_6$ alkyl groups, for example 2,2,2-trichloroethyl; $C_2$-$C_4$ alkenyl groups, for example allyl; optionally substituted aryl groups, for example phenyl and p-nitro-phenyl; optionally substituted aryl-$C_1$-$C_6$ alkyl groups, for example benzyl, p-nitro-benzyl and p-methoxy-benzyl; aryloxy-$C_1$-$C_6$ alkyl groups, for example phenoxy-methyl; or groups such as benzhydryl, o-nitro-benzhydryl, acetonyl, trimethylsilyl, diphenyl-tert-butyl-silyl, and dimethyl-tert-butyl-silyl; or groups such as pivaloyloxy methyl or phtalidyl.

Particularly preferred carboxy protecting groups are allyl, p-nitrobenzyl, trimethylsilyl, dimethyl-tert-butylsilyl, an trichloroethyl.

Preferably in the compound of formula (IV) R is a $C_1$-$C_3$-alkyl group substituted by a protected hydroxy and a particularly preferred hydroxy protecting group is dimethyl-tert-butyl-silyl.

The reaction between a compound of formula (II) and a compound of formula (III), may be performed in a suitable organic, preferably aprotic, solvent which may be, for instance, tetrahydrofuran, dimethylformamide, acetone or a halogenated hydrocarbon such as, e.g., dichloromethane. The reaction temperature may, preferably, vary between about $-70°$ C. and about $+25°$ C., preferably between $-40°$ C. and $+15°$ C.

A compound of formula (III) wherein L is a sulphonyloxy group may be prepared reacting, according to known and conventional procedures, a hydroxymethyl penem precursor of formula (V)

$$\text{(V)}$$

wherein R and Z' are as defined above, with the appropriate sulphonyl anhydride or sulphonyl halide, preferably triflic anhydride, a triflic chloride, in the presence of a non-nucleophilic acid acceptor which may be, for instance, an inorganic base such as, e.g., calcium or lithium carbonate or calcium oxide, or an organic base such as, e.g., 2,6-lutidine or also the same pyridine compound of formula (II) to be reacted in the subsequent step.

Indeed, according to a preferred procedure of the invention the compound of formula (V) is made to react with the suitable sulphonyl anhydride or sulphonyl halide in the presence of an excess, usually an amount equal to or greater than 2 molar equivalents, of the desired compound of formula (II): in this situation the compound of formula (III) is not even isolated from the reaction mixture because it reacts in situ with the pyridine compound of formula (II).

The hereabove said preferred procedure is preferably carried out using dry dichloromethane as solvent at temperatures from about −40° C. to about 0° C.

When a compound of formula (II) is reacted with a compound of formula (III) wherein L is halogen, particularly chlorine, the presence of a silver salt soluble in the media, e.g. $AgClO_4$, may be beneficial.

A compound of formula (III) wherein L is halogen, in particular chlorine, may be, e.g., prepared from the corresponding hydroxymethyl penem precursors of formula (V) according to a modified Mitsunobu reaction in which the carbinol of formula (V) is allowed to react with an organic amine hydrohalide, preferably an organic amine hydrochloride such as, for instance, methoxyamine hydrochloride or pyridine hydrochloride, and the preformed complex obtained from diethylazodicarboxylate and triphenylphosphine, the said reaction being carried out, e.g., in tetrahydrofuran or methylene chloride, preferably at room temperature.

With particularly inert pyridines of formula (II) it may be preferable to perform the displacement reaction on a 2-thia-cephem compound of formula (IV) rather than on a penem derivative of formula (III). The reaction is then carried out in an inert organic solvent, such as, for instance, dichloromethane, tetrahydrofuran, dimethylsulphoxide or dimethylacetamide, and optionally in the presence of a iodide salt, e.g. NaI, or with a silver salt, e.g. $AgClO_4$, at temperature ranging from about −15° C. to about +50° C., to obtain a 2-thiacephem intermediate of formula (VI)

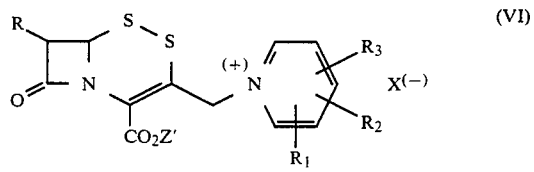

(VI)

wherein R, $R_1$, $R_2$, $R_3$ and Z' are as defined above, and $X^{(-)}$ is a counterion, such as, e.g., depending on the reaction and work-up conditions, $Br^{(-)}$, $I^{(-)}$, $ClO_4^{(-)}$, $^{(-)}OCOCH_3$, and such compound of formula (VI) is then, in any order, desulphurized and deprotected to obtain the desired compound of formula (I).

A suitable desulphurizing agent is triphenylphosphine: see, for example, E. Perrone et al, Tetrahedron Lett., 24, 1631 (1983). Other desulphuration conditions which can be applied on 2-thiacephems of formula (VI) to give, after removal of the protecting group in Z', penems of formula (I), are object of UK Patent Application No. 2,131,432 A.

Removal of the protecting groups can be effected by known per se procedures; e.g. silyl groups can be removed under mild acidic conditions, or by fluoride ions, e.g. with tetrabutylammonium fluoride; p-nitrobenzyl groups can be removed by reduction, e.g. by catalytic hydrogenation, or with metals, such as Fe and Zn; allyl carboxylates can be cleaved by transallylation with an organic acid or a salt thereof, such as acetic acid, 2-ethylhexanoic acid, or their sodium and potassium salts, this reaction being catalyzed by a triphenylphosphine-palladium complex, preferably by tetrakis-triphenylphosphine-Pd°.

The optional salification of an obtained compound and the separation of a mixture of isomers into the single isomers may be carried out following known and conventional procedures.

The pyridines of formula (II) are known compounds, or can be prepared from known compounds by known methods. Intermediates of formula (V) have been described in UK Patent Specification No. 2,111,496; intermediates of formula (IV) have been described in UK Patent Application No. 2,131,432 A.

The compounds of formula (I) provided by the present invention are potent, broad spectrum, antibacterial agents.

Although we had disclosed unsubstituted pyridinio congeners in our UK Patent Application No. 2,118,181 A and found for these compounds very interesting pharmacokinetic properties, the antibacterial potency displayed by the compounds of the present invention, particularly on Gram-negative strains, was totally unexpected and contrary to commonly accepted activity-lipophilicity correlations.

The following table shows the activity of a typical compound of formula (I), the "Compound 1" of the previous table, in comparison with the activity of the corresponding unsubstituted pyridinio analog.

| Comparison between the antibacterial in vitro activity (MIC, μg/ml) of "compound 1" and the unsubstituted pyridinio analog | | |
|---|---|---|
| Organism | "Compound 1"[a] | Unsubstituted[b] pyridinio analog |
| Staphylococcus aureus Smith | 0.005 | 0.015 |
| Staphylococcus aureus 39/2 | 0.005 | 0.01 |
| Streptococcus pyogenes ATCC 12384 | 0.0007 | 0.01 |
| Klebsiella aerogenes 1522 E | 0.27 | 5.7 |
| Klebsiella aerogenes 1082 E | 0.27 | 16 |
| Enterobacter cloacae 1321 E | 0.18 | 4 |
| Escherichia coli B | 0.13 | 8 |
| Escherichia coli 026:B6 | 0.044 | 4 |
| Salmonella typhimurium ATCC 14028 | 0.18 | 1 |
| Proteus morganii ATCC 25830 | 1.55 | 32 |
| Pseudomonas aeruginosa ATCC 19660 | 50 | 11.3 |

[a]"Compound 1": (5R,6S)-6-[(1R)-hydroxyethyl]-2-[1-(5-ethyl-2-methyl)-pyridinio]-methyl-penem-3-carboxylate
[b]Unsubstituted pyridinio analog: (5R,6S)-6-[(1R)-hydroxy-ethyl]-2-(1-pyridinio)-methyl-penem-3-carboxylate.

Moreover, it has been found that the compounds of formula (I) of the present invention are scarcely bound to the serum proteins.

A number of them, for example "Compound 2", are remarkably active against Pseudomonas aeruginosa strains. When tested in vivo after parenteral administration, these compounds showed a very high degree of therapeutic effectiveness in treating infections caused by both Gram-positive and Gram-negative bacteria, their toxicity being, on the other hand, quite negligible.

Owing to their high antibacterial activity the compounds of the invention are thus useful, for example, in the treatment of respiratory tract infections, for example, bronchitis, bronchopneumonia, pleuritis; hepatobiliary and abdominal infections, septicemia; urinary tract infections, for example, pyelonephritis, cystitis; obstetrical and gynecological infections, for instance, cervicitis, endometritis; ear, nose and throat infections, for instance otitis, sinusitis, parotitis.

The compounds of the invention may be administered, either to humans or to animals, in a variety of dosage forms, e.g., orally in the form of tablets, capsules, drops or syrups; rectally in the form of suppositories; parenterally, e.g., intravenously or intramuscularly (as solutions or suspensions), with intravenous administration being preferred in emergency situation; by inhalation in the form of areosols or solutions for nebulizers; intravaginally in the form, e.g., of bougies; or topically in the form of lotions, creams and ointments. The pharmaceutical or veterinary compositions containing the compounds of formula (I), which are too within the scope of the invention, may be prepared in a conventional way by employing the conventional carriers or diluents used for, e.g., cephalosporins. Conventional carriers or diluents are, for example, water, gelatine, lactose, starches, magnesium stearate, talc, vegetable oils, cellulose and the like. Daily doses in the range of about 0.5 to about 80 mg per kg of body weight may be used, in various animal species, the exact dose depending on the age, weight and condition of the subject to be treated and on the frequency and route of administration. A preferred way of administration of the compounds of the invention is the parenteral one: in this case the compounds may be administered, for example, to adult humans 1–4 times a day, dissolved in a suitable solvent, such as, for example, sterile water or lidocaine hydrochloride solution for intramuscular injections, and sterile water, physiological saline solution, dextrose solution or the conventional intravenous fluids or electrolytes for intravenous injections.

The following examples illustrate but do not limit the present invention.

EXAMPLE 1

(5R,6S)-6-[(1R)-hydroxyethyl]-2-[1-(3-cyanomethyl)-pyridino]-methylpenem-3-carboxylate A solution of p-nitrobenzyl-(5R,6S)-6-[(1R)-p-nitrobenzyloxycarbonyloxyethyl]-2-hydroxymethyl-penem-3-carboxylate (300 mg) in dry, ethanol-free, dichloromethane (30 ml) was treated at −35° C. under nitrogen with (3-pyridyl)acetonitrile (0.3 ml) and, immediately after, with trifluoromethanesulphonic anhydride (0.17 ml). After 20 minutes at −35° C. and 15 minutes at −5° C., 0.1M aqueous HCl (20 ml) was added under stirring. The organic layer was separated, washed again with 0.1M HCl, then dried over MgSO$_4$, treated with charcoal, filtered and evaporated. The obtained residue was dissolved in tetrahydrofuran (13 ml) and mixed with a solution of ammonium chloride (3.3 g) in water (13 ml).

The mixture was stirred vigorously with iron powder (2 g), added in 3 portions at 15 minute intervals. After 90 minutes, the suspension was filtered, freed at ≦15° C. from most of the organic solvent, and immediately washed with ethyl ether and then with ethyl acetate. The aqueous phase was briefly treated with charcoal, concentrated and passed through a reverse phase column (LiChroprep RP-18) eluting first with distilled water, then with water-MeCN (up to 20% in the latter). The product-containing fractions (TLC Kieselgel 60 Merck; eluants H$_2$O—MeOH—NaCl 9:1:1; Rf 0.44) were freeze-dried, thus affording 45 mg of the title compound, NMR (200 MHz, D$_2$O): δp.p.m.: 1.28 (3H, d, J=6.4 Hz, CH$_3$—CH); 3.99 (1H, dd, J=1.4 and 6.0 Hz, H-6); 4.24 (1H, dq, J=6.0 and 6.4 Hz, H-8); 4.30 (2H, s, CH$_2$CN); 5.70 (1H, d, J=1.4 Hz, H-5); 5.97 (2H, ABq, J=14.7 Hz, CH$_2$N+);

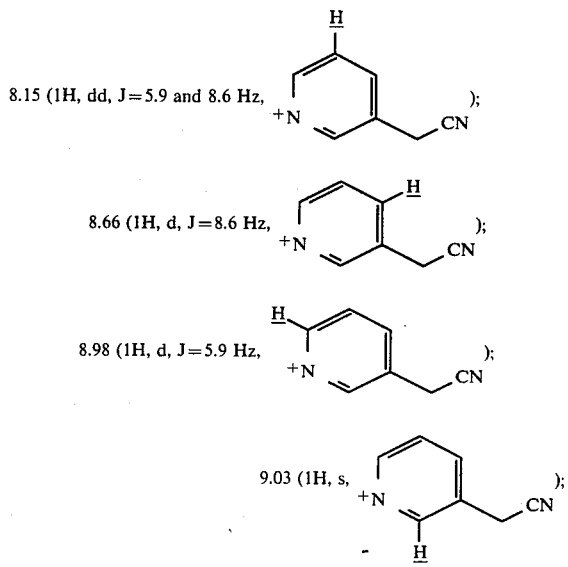

8.15 (1H, dd, J=5.9 and 8.6 Hz, );

8.66 (1H, d, J=8.6 Hz, );

8.98 (1H, d, J=5.9 Hz, );

9.03 (1H, s, );

λmax (H$_2$O) nm(ε): 262 (7,422) and 312 (4,401).

By analogous procedure the following compounds were prepared:

(5R,6S)-6-[(1R)-hydroxyethyl]-2-[1-(2-cyanomethyl)-pyridinio]-methyl-penem-3-carboxylate;

(5R,6S)-6-[(1R)-hydroxyethyl]-2-[1-(3-chloro)-pyridinio]-methyl-penem-3-carboxylate;

(5R,6S)-6-[(1R)-hydroxyethyl]-2-[1-(2-chloro-4-methyl)-pyridinio]-methyl-penem-3-carboxylate;

(5R,6S)-6-[(1R)-hydroxyethyl]-2-[1-(3-hydroxy)-pyridinio]-methyl-penem-3-carboxylate.

EXAMPLE 2

(5R,6S)-6-[(1R)-hydroxyethyl]-2-[1-(2-methyl-5-ethyl)-pyridinio]-methylpenem-3-carboxylate A solution of allyl-(5R,6S)-6-[(1R)-tert-butyldimethylsilyloxyethyl]-2-hydroxymethylpenem-3-carboxylate (600 mg) in dry dichloromethane (20 ml) was treated with 5-ethyl-2-methylpyridine (1.19 ml), followed by trifluoromethane sulphonic anhydride (0.5 ml) at −30° C. After depletion of the starting penem carbinol (TLC monitoring, ethyl acetate-cyclohexane 2:1), 0.1M aqueous HCl was added.

The organic layer was separated, washed with water, evaporated and purified by pressure chromatography (Kieselgel 60 Merck 230–400 mesh) on a short-path column.

By-products were eluted out with ethyl acetate-cyclohexane mixtures; salts (chloride and/or trifluoromethanesulphonate) of allyl (5R,6S)-6-[(1R)-tert-butyldimethylsilyloxyethyl]-2-[1-(5-ethyl-2-methyl)-pyridinio]-methylpenem-3-carboxylate (480 mg) were recovered after elution with ethyl acetate-ethanol mixtures; νmax (CHCl$_3$) 1795, 1700 cm$^{-1}$. This product (300 mg) was dissolved in a mixture of tetrahydrofuran (10 ml) and acetic acid (1 ml), and left overnight in the presence of tetrabutylammonium fluoride trihydrate (0.9 g), after which time the solution was put on the top of a silica gel column (SiO$_2$) 230–400 Mesh, φ=1.5 cm, h=10 cm) packed with dichloromethane. The tetrabutylammonium salts were eluted with CH₂Cl₂/MeOH mixtures, while further elution with neat methanol and methanol-water (1:2) gave the acetate of allyl-(5R,6S)-6-[(1R)-hydroxyethyl]-2-[1-(2-methyl-5-ethyl)-pyridinio]-methylpenem-3-carboxylate (160 mg), νmax (CHCl₃): 3300, 1790, 1705 cm⁻¹; λmax (CHCl₃): 277 and 330 nm. This intermediate (80 mg) was dissolved in dichloromethane (3 ml). Acetic acid (0.1 ml), triphenylphosphine (20 mg) and tetrakis (triphenylphosphine)palladium (O) (20 mg) were added, and the progress of the deallylation reaction monitored by TLC (isopropanol-acetic acid-water, 5:1:1).

After the starting material had disappeared, the solvent was evaporated and the residue triturated with ethyl acetate (3 times). The undissolved material was taken up in distilled water and the solution was passed through a LiChroprep RP-18 reverse phase column, eluting first with water, then with 20% MeCN in water. The appropriate fractions (TLC monitoring; Kieselgel 60 Merck, H₂O—MeOH—NaCl 9:1:1 as eluants) were collected and freeze-dried, affording 45 mg of the title product, NMR (200 MHz, D₂O): δp.p.m.: 1.26 (3H, d, J=6.5 Hz, C̲H̲₃CH); 1.27 (3H, t, J=7.5 Hz, CH₂C̲H̲₃); 2.78 (3H, s, C̲H̲₃); 2.82 (2H, q, J=7.5 Hz, C̲H̲₂CH₃); 3.93 (1H, dd, J=1.5 and 5.8 Hz, H-6); 4.22 (1H, dq, J=5.8 and 6.5 Hz, H-8); 5.66 (1H, d, J=1.5 Hz, H-5); 5.93 (2H, ABq, J=16.2 Hz, CH₂N⁺);

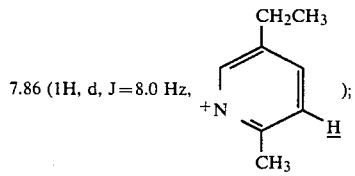

7.86 (1H, d, J=8.0 Hz, 8.31 (1H, dd, J=1.8 and 8.0 Hz, 8.67 (1H, d, J=1.8 Hz,

λmax (H₂O) nm(ε): 274(10,177) and 312 (4,680).

By analogous procedure the following compounds were prepared:

(5R,6S)-6-[(1R)-hydroxyethyl]-2-[1-(4-methoxy)-pyridinio]-methyl-penem-3-carboxylate, NMR (60 MHz, D₂O): δp.p.m.: 1.25 (3H, d, J=6.5 Hz, C̲H̲₃CH), 3.90 (1H, dd, J=1.5 and 6 Hz, H-6), 3.98 (3H, s, OCH₃), 4.22 (1H, m, H-8), 5.65 (1H, d, J=1.5 Hz, H-5), 5.85 (2H, ABq, J=14.4 Hz, CH₂N⁺), 7.80-8.50 (4H, m, AZ);

(5R,6S)-6-[(1R)-hydroxyethyl]-2-[1-(4-methylthio)-pyridinio]-methyl-penem-3-carboxylate, NMR (60 MHz, D₂O): δp.p.m.: 1.24 (3H, d, J=6.3 Hz, C̲H̲₃CH), 2.65 (3H, s, SCH₃), 3.95 (1H, dd, J=1.2 and 6 Hz, H-6), 4.20 (1H, m, H-8), 5.70 (1H, d, J=1.2 Hz, H-5), 5.85 (2H, ABq, J=14.6 Hz, CH₂N⁺), 7.70 (2H, d, J=7.1 Hz, 8.40 (2H, d, J=7.1 Hz, (5R,6S)-6-[(1R)-hydroxyethyl]-2-[1-(3-methoxy)-pyridinio]-methyl-penem-3-carboxylate, NMR (60 MHz, D₂O): δp.p.m: 1.25 (3H, d, J=6.5 Hz, C̲H̲₃CH), 3.95 (4H, m, OCH₃ and H-6), 4.25 (1H, m, H-8), 5.65 (1H, d, J=1.5 Hz, H-5), 5.90 (2H, ABq, J=15 Hz, CH₂N⁺), 7.7-8.2 (2H, m,     ), 8.3-8.7 (2H, m, (5R,6S)-6-[(1R)-hydroxyethyl]-2-[1-(3-methylthio)-pyridinio]-methyl-penem-3-carboxylate, NMR (60 MHz, D₂O): δp.p.m: 1.26 (3H, d, J=6.5 Hz, C̲H̲₃—CH), 2.64 (3H, s, SCH₃), 3.98 (1H, dd, J=1.5 and 6 Hz, H-6), 4.25 (1H, m, H-8), 5.65 (1H, d, J=1.5 Hz, H-5), 5.85 (2H, ABq, J=14.4 Hz, CH₂N⁺), 7.80-8.50 (4H, m, Az); and (5R,6S)-6-[(1R)-hydroxyethyl]-2-[1-(4-sulphoethyl)-pyridinio]-methyl-penem-3-carboxylate.

EXAMPLE 3

(5R,6S)-6-[(1R)-hydroxyethyl]-2-[1-(3,5-dimethyl)-pyridinio]-methylpenem-3-carboxylate p-Nitrobenzyl (5R,6S)-6-[(1R)-p-nitrobenzyloxycarbonyloxyethyl]-2-hydroxymethylpenem-3-carboxylate (300 mg) in dichloromethane (10 ml) was treated in a nitrogen atmosphere with 3,5-lutidine (0.3 ml) and trifluoromethanesulphonic anhydride (0.17 ml) at −40° C. After 15 minutes, 0.1M aqueous HCl was added and the organic layer was further washed with 0.1M HCl and water. Upon evaporation, a brownish foam (0.34 g) was obtained, which was dissolved in a minimum amount of chloroform and added dropwise under stirring to ethyl ether. A fine, cream powder separated (0.26 g), which was collected, dissolved in tetrahydrofuran (15 ml), mixed to a solution of NH₄Cl (3.3 g) in water (15 ml) and vigorously stirred with iron powder (3 g in two portions at 30 minute intervals) at 4°–5° C.

The reaction mixture was filtered, the organic solvent evaporated and the aqueous solution washed with ethyl acetate, treated with charcoal, filtered, concentrated and passed through a reverse-phase column. After eluting the inorganic salts with distilled water, the product was collected with a gradient of acetonitrile in water (45 mg), NMR (200 MHz, D₂O): δp.p.m.: 1.27 (3H, d, J=6.4 Hz, C̲H̲₃CH); 2.49 (6H, s, CH₃ on pyridinio; 3.95 (1H, dd, J=1.5 and 5.9 Hz, H-6); 4.23 (1H, dq, J=5.9 and 6.4 Hz, H-8); 5.84 (2H, ABq, J=14.9 Hz, CH$_2$N$^+$); 5.67 (1H, d, J=1.5 Hz, H-5);

8.24 (1H, s, 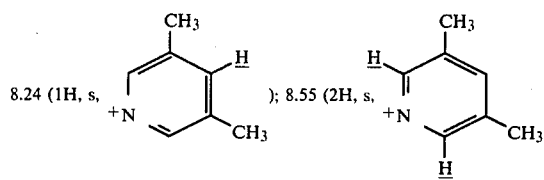); 8.55 (2H, s, );

λmax (H$_2$O) nm(ε): 270.

By analogous procedure the following compounds were prepared:

(5R,6S)-6-[(1R)-hydroxyethyl]-2-[1-(3-methyl)-pyridinio]-methyl-penem-3-carboxylate, NMR (200 MHz, D$_2$O): δp.p.m: 1.26 (3H, d, J=6.5 Hz, $\underline{CH_3}$CH), 2.54 (3H, s, CH$_3$), 3.96 (1H, dd, J=1.4 and 5.7 Hz, H-6), 4.22 (1H, m, H-8), 5.67 (1H, d, J=1.4 Hz, H-5), 5.88 (2H, ABq, J=14.8 Hz, CH$_2$N$^+$), 7.95 (1H, m, 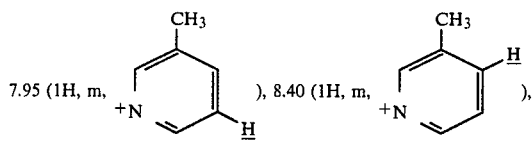), 8.40 (1H, m, ), 8.73 (2H, m, 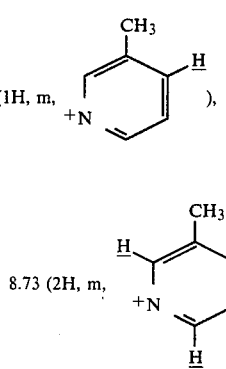);

UV (H$_2$O): λ$_{max}$ 266 and 314 nm;

(5R,6S)-6-[(1R)-hydroxyethyl]-2-[1-(3-amino)-pyridinio]-methyl-penem-3-carboxylate; and (5R,6S)-6-[(1R)-hydroxyethyl]-2-[1-(3-dimethylamino)-pyridinio]-methyl-penem-3-carboxylate.

We claim:

1. A compound of the following formula (I)

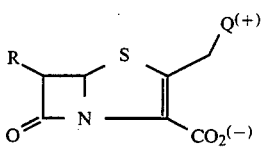

wherein
R is a C$_1$-C$_3$ alkyl group substituted by a hydroxy group;
Q$^{(+)}$ represents a group wherein R$_1$ is C$_1$-C$_4$ alkyl group either unsubstituted or substituted by a group —C≡N, and R$_2$ is hydrogen or C$_1$-C$_4$ alkyl.

2. A compound having the formula (I) reported in claim 1, wherein R is (α-hydroxy)ethyl; R$_1$ is methyl either unsubstituted or substituted by a group —C≡N, and R$_2$ is hydrogen or C$_1$-C$_2$-alkyl.

3. A compound having the formula (I) reported in claim 1 wherein
R is (α-hydroxy)ethyl;
R$_1$ is methyl or cyanomethyl, and
R$_2$ is hydrogen, methyl or ethyl.

4. A compound chosen from:
(5R,6S)-6-[(1R)-hydroxyethyl]-2-[1-(3-cyanomethyl)-pyridinio]-methyl-penem-3-carboxylate;
(5R,6S)-6-[(1R)-hydroxyethyl]-2-[1-(2-methyl-5-ethyl)-pyridinio]-methyl-penem-3-carboxylate;
(5R,6S)-6-[(1R)-hydroxyethyl]-2-[1-(3,5-dimethyl)-pyridinio]-methyl-penem-3-carboxylate; and
(5R,6S)-6-[(1R)-hydroxyethyl]-2-[1-(3-methyl)-pyridinio]-methyl-penem-3-carboxylate.

5. An antibacterial pharmaceutical composition containing a suitable carrier and/or diluent and, as the active principle, an effective amount of a compound according to claim 1.

6. A method of producing antibacterial effect in a patient in need of it, said method comprising administering to said patient a therapeutically effective amount of a compound of claim 1.

7. A method of producing antibacterial effect in a patient in need of it, said method comprising administering to said patient a therapeutically effective amount of a composition of claim 5.

* * * * *